United States Patent
Smith et al.

(10) Patent No.: US 9,669,202 B2
(45) Date of Patent: Jun. 6, 2017

(54) DRUG DELIVERY DEVICE AND SET OF A DRUG DELIVERY DEVICE AND A PLURALITY OF MOUNTABLE ELEMENTS

(75) Inventors: Christopher Smith, Holmes Chapel (GB); Matthew Ekman, Macclesfield (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 13/382,497

(22) PCT Filed: Jul. 2, 2010

(86) PCT No.: PCT/EP2010/059425
§ 371 (c)(1),
(2), (4) Date: Jun. 6, 2012

(87) PCT Pub. No.: WO2011/003817
PCT Pub. Date: Jan. 13, 2011

(65) Prior Publication Data
US 2012/0238960 A1    Sep. 20, 2012

(30) Foreign Application Priority Data

Jul. 7, 2009  (EP) ..................................... 09008852

(51) Int. Cl.
*A61M 5/31* (2006.01)
*A61M 37/00* (2006.01)
(Continued)

(52) U.S. Cl.
CPC ............ *A61M 37/00* (2013.01); *A61M 35/00* (2013.01); *A61M 5/003* (2013.01); *A61M 2005/3125* (2013.01)

(58) Field of Classification Search
CPC .......... A61M 2205/583; A61M 5/3129; A61M 2005/3125; A61M 5/24; A61M 5/31525; A61M 5/31548; A61M 5/31546
(Continued)

(56) References Cited

U.S. PATENT DOCUMENTS 5,279,585 A * 1/1994 Balkwill ............. A61M 5/3158
                                                    222/309
5,279,586 A * 1/1994 Balkwill ............. A61M 5/3158
                                                    222/309
(Continued)

FOREIGN PATENT DOCUMENTS

DE    19519147 A1    12/1995
DE    20110690      9/2001
(Continued)

OTHER PUBLICATIONS

European Search Report for European App. No. 09008852, dated Oct. 2, 2009.
(Continued)

*Primary Examiner* — Edelmira Bosques
*Assistant Examiner* — Matthew A Engel
(74) *Attorney, Agent, or Firm* — McDonnell Boehnen Hulbert & Berghoff LLP

(57) ABSTRACT

A drug delivery device is configured to receive a cartridge containing a drug. The drug delivery device comprises a content display for displaying information related to one of the cartridge and the drug contained in the cartridge. The content display is configured to selectively display at least two different pieces of information and is configured to be adjusted mechanically to display one of the pieces of information. Furthermore, a set of the drug delivery device and a plurality of mountable elements is provided, wherein the mountable elements differ in their shapes and wherein the (Continued)

displayed piece of information is specific for the shape of the mountable element.

13 Claims, 9 Drawing Sheets

(51) Int. Cl.
*A61M 35/00* (2006.01)
*A61M 5/00* (2006.01)

(58) Field of Classification Search
USPC ............ 604/207, 209, 211, 189; 128/200.14
See application file for complete search history.

(56) References Cited

U.S. PATENT DOCUMENTS

| | | | |
|---|---|---|---|
| 5,431,627 A | 7/1995 | Pastrone et al. | |
| 5,693,027 A * | 12/1997 | Hansen | A61M 5/24 604/200 |
| 5,728,074 A * | 3/1998 | Castellano | G06F 19/3468 600/309 |
| 8,001,963 B2 * | 8/2011 | Giroux | A61M 15/08 128/200.14 |
| 8,202,255 B2 * | 6/2012 | Saiki | A61M 5/31551 604/181 |
| 8,298,194 B2 * | 10/2012 | Moller | A61M 5/24 604/181 |
| 8,348,904 B2 * | 1/2013 | Petersen | A61M 5/24 604/207 |
| 2002/0022821 A1 * | 2/2002 | Eilersen | G06K 7/10 604/404 |
| 2002/0165500 A1 * | 11/2002 | Bechtold | A61M 5/2033 604/209 |
| 2003/0078195 A1 | 4/2003 | Kristensen et al. | |
| 2007/0197978 A1 | 8/2007 | Wortham | |
| 2008/0051692 A1 * | 2/2008 | Petersen | A61N 1/303 604/20 |
| 2008/0171995 A1 * | 7/2008 | Vitullo | A61M 5/28 604/187 |
| 2008/0287785 A1 | 11/2008 | Saitoh et al. | |
| 2009/0053085 A1 | 2/2009 | Thompson et al. | |
| 2009/0062728 A1 * | 3/2009 | Woo | A61M 5/1723 604/66 |
| 2009/0062730 A1 * | 3/2009 | Woo | A61M 5/1723 604/66 |
| 2012/0071834 A1 * | 3/2012 | Harms | A61M 5/3129 604/189 |
| 2012/0089098 A1 * | 4/2012 | Boyd | A61M 5/24 604/189 |
| 2012/0101445 A1 * | 4/2012 | Jansen | A61M 5/24 604/189 |
| 2012/0232517 A1 * | 9/2012 | Saiki | A61M 5/31551 604/500 |
| 2012/0253288 A1 * | 10/2012 | Dasbach | A61J 7/04 604/189 |
| 2012/0310172 A1 * | 12/2012 | MacDonald | A61M 5/31525 604/207 |
| 2012/0330228 A1 * | 12/2012 | Day | A61M 5/14244 604/82 |
| 2013/0072897 A1 * | 3/2013 | Day | A61M 5/1452 604/500 |
| 2013/0079708 A1 * | 3/2013 | Wimpenny | A61M 5/002 604/65 |
| 2013/0096511 A1 * | 4/2013 | MacArthur | A61J 1/06 604/189 |
| 2013/0131601 A1 * | 5/2013 | Pommereau | A61M 5/3129 604/189 |
| 2013/0226095 A1 * | 8/2013 | Dasbach | A61J 7/04 604/189 |

FOREIGN PATENT DOCUMENTS

| | | |
|---|---|---|
| EP | 0362484 | 4/1990 |
| EP | 1832305 | 9/2007 |
| JP | H07-250895 A | 10/1995 |
| JP | 2007-159717 A | 6/2007 |
| JP | 2010-510011 A | 4/2010 |
| WO | 02/092153 | 11/2002 |
| WO | 03/028790 | 4/2003 |
| WO | 03/086511 A1 | 10/2003 |
| WO | 2005/004954 | 1/2005 |
| WO | 2005/075010 | 8/2005 |
| WO | 2005/097232 A1 | 10/2005 |
| WO | 2006/084464 | 8/2006 |
| WO | 2008/042701 A2 | 4/2008 |
| WO | 2008/062025 A1 | 5/2008 |

OTHER PUBLICATIONS

International Search Report and Written Opinion for International App. No. PCT/EP2010/059425, mailed Jul. 30, 2010.
International Preliminary Report on Patentability for Int. App. No. PCT/EP2010/059425, issued Jan. 10, 2012.
Japanese Office Action for JP Application No. 2015-081367, dated Mar. 22, 2016.

* cited by examiner

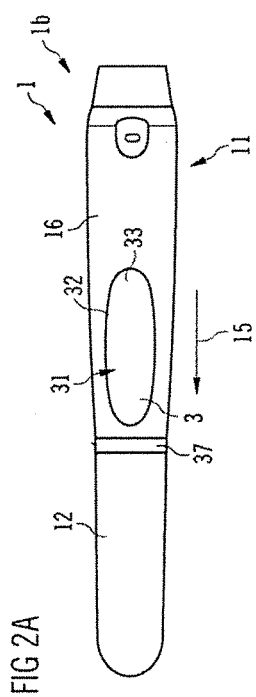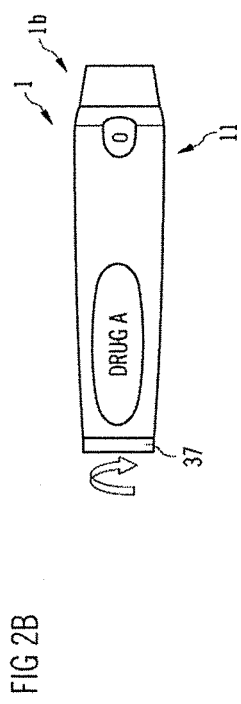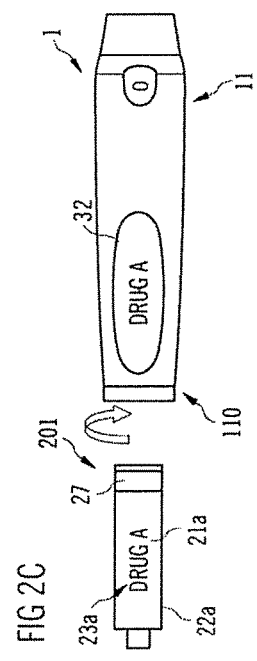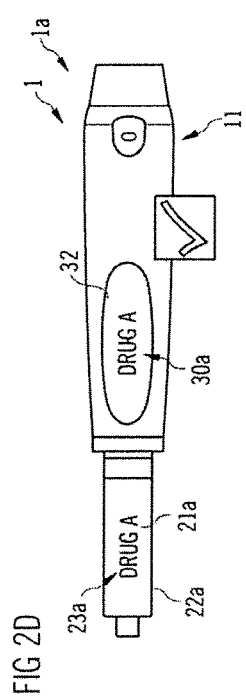

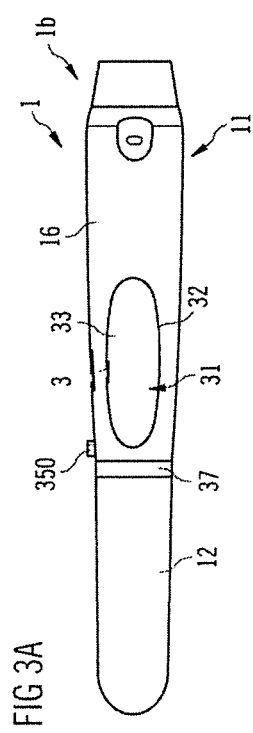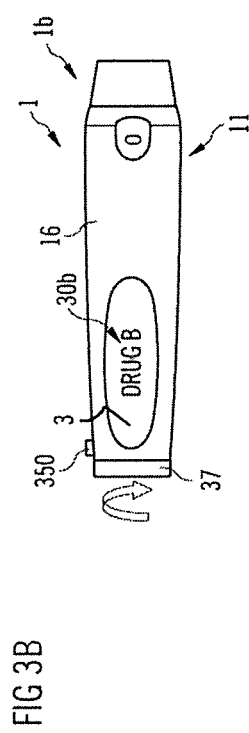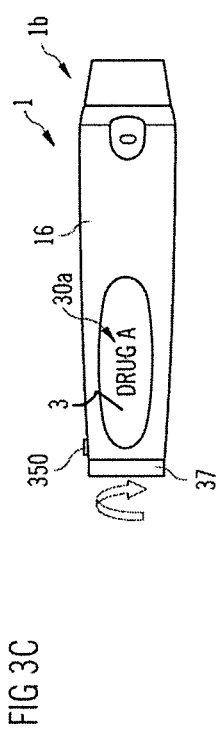

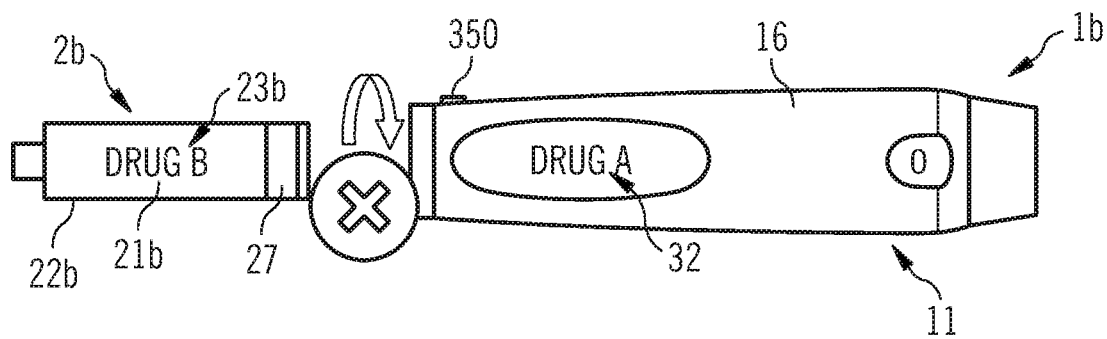
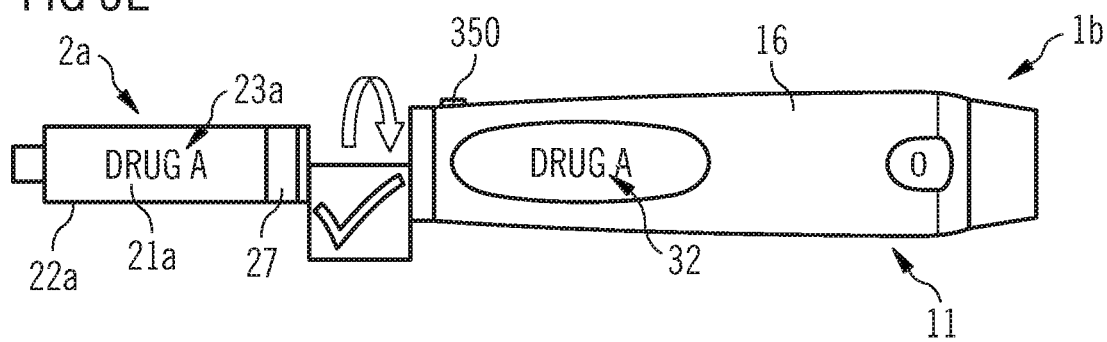
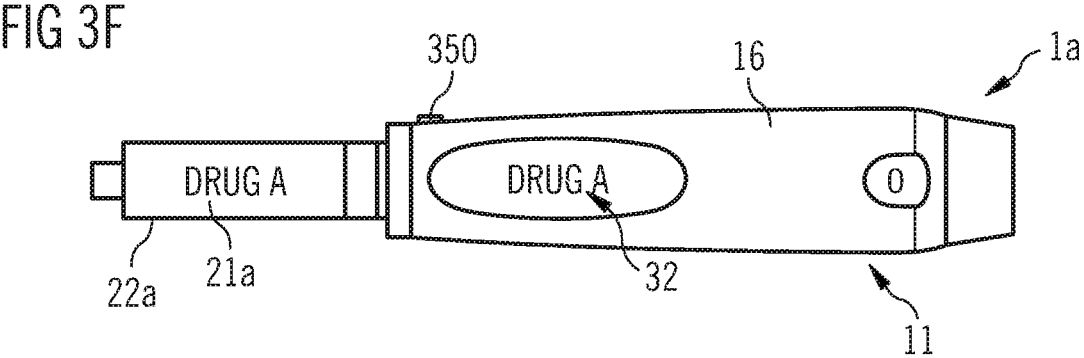
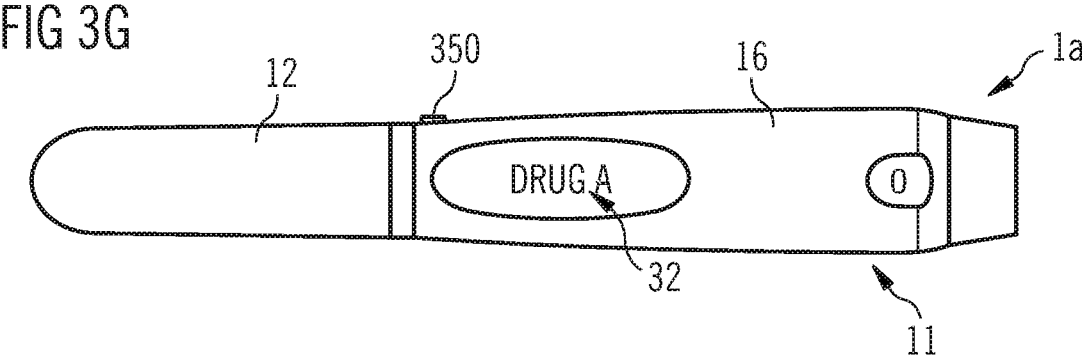

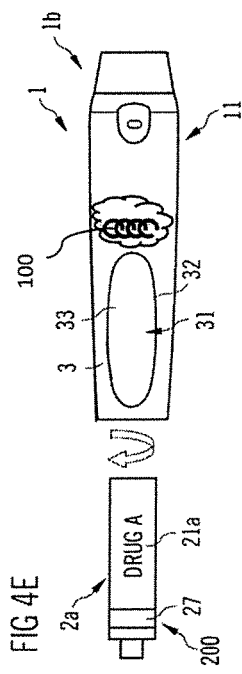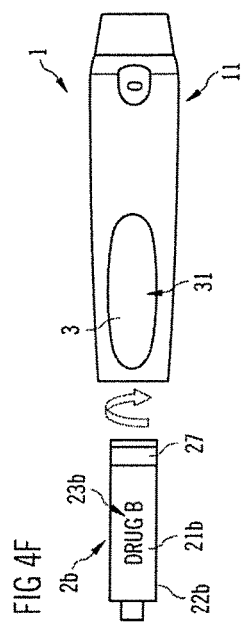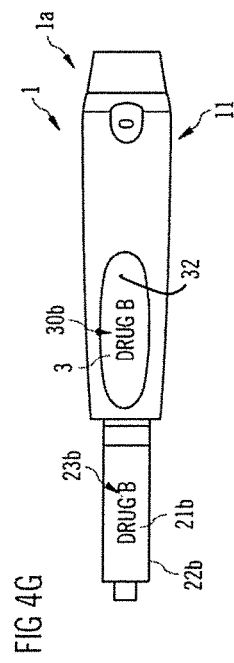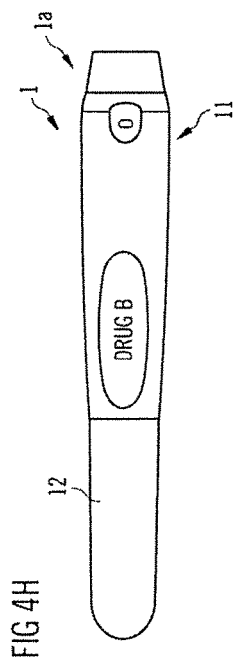

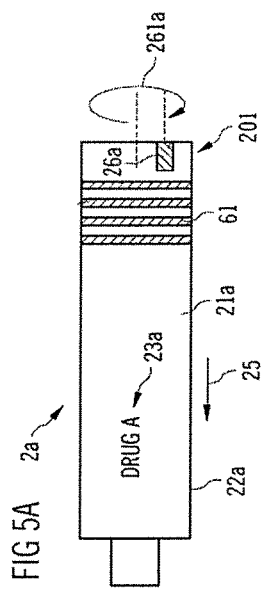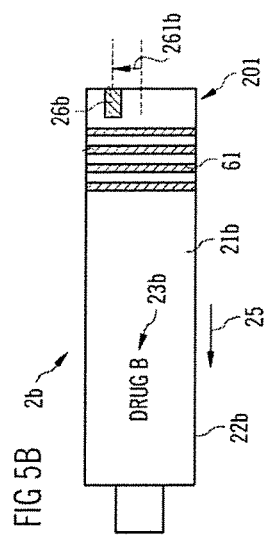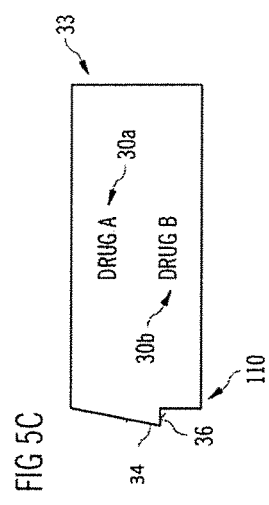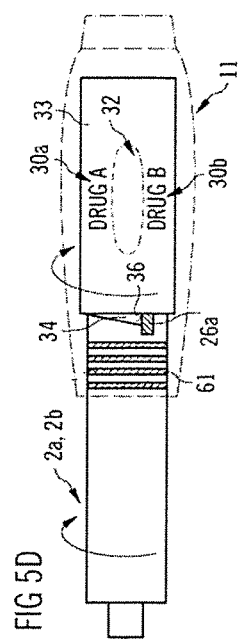

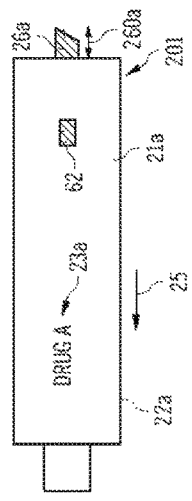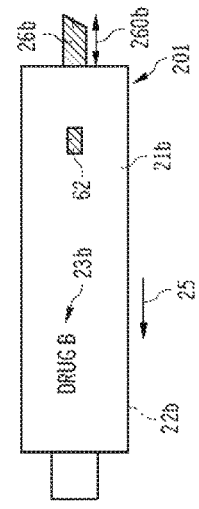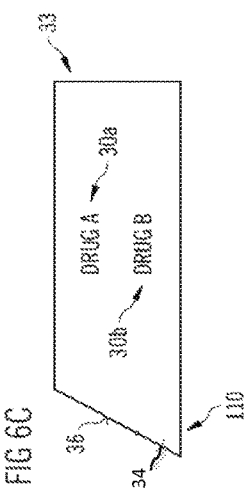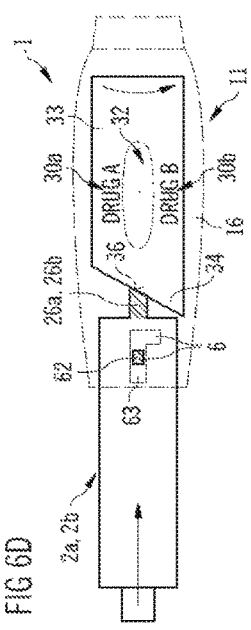

DRUG DELIVERY DEVICE AND SET OF A DRUG DELIVERY DEVICE AND A PLURALITY OF MOUNTABLE ELEMENTS

CROSS REFERENCE TO RELATED APPLICATIONS

The present application is a U.S. National Phase Application pursuant to 35 U.S.C. §371 of International Application No. PCT/EP2010/059425 filed Jul. 2, 2010, which claims priority to European Patent Application No. 09008852.7 filed on Jul. 7, 2009. The entire disclosure contents of these applications are herewith incorporated by reference into the present application.

FIELD OF INVENTION

This disclosure relates to a drug delivery device for use with a cartridge containing a drug. In particular, it relates to a drug delivery device being useable with different types of cartridges or cartridges containing different drugs or different compositions of drugs. For such a device, there may be a potential risk that a user has a wrong assumption of the specific cartridge mounted in the device and, therefore, the user may inadvertently administer a wrong drug.

BACKGROUND

The international patent applications WO 02/092153 A2, WO 03/028790 A1, WO 2005/075010 A1, WO 2006/084464 and the European patent application EP 0362484 A2 disclose drug delivery devices comprising means for reading information provided on a cartridge mounted in the device. The information is displayed by an electronic device, such as an LCD-display.

The international patent application WO 2005/004954 A1 discloses a drug delivery device usable with cartridges containing different concentrations of a drug. The drug delivery device comprises means for adjusting the delivery mechanism to a specific concentration of the drug. The preset concentration is displayed by an LCD-display.

It is an aim of the present invention to provide a drug delivery device, wherein a user is easily and reliably provided with information related to a cartridge mountable in the device or a drug contained in such a cartridge.

SUMMARY

According to a first aspect of the disclosure, a drug delivery device configured to receive a cartridge containing a drug is provided. The drug delivery device comprises a content display for displaying information related to one of the cartridge and a drug contained in the cartridge. The content display is configured to selectively display at least two different pieces of information and is configured to be adjusted mechanically to display one of the pieces of information.

The disclosed drug delivery device may be useable with two or more different types of cartridges or cartridges differing in the drug or composition of drugs contained therein. Thereby, a user administering different drugs may only need a single drug delivery device.

In one embodiment, the drug delivery device is a reusable device such that a cartridge mounted in the device can be exchanged. As an example, the device may be used by a patient for self-administering of drugs. The same device may be used for administering different drugs. Here, for each delivery action, the appropriate cartridge can be inserted in the device. The device may be also used for administering only one drug. Here, a new cartridge can be inserted in the device if the used cartridge is empty or if the medicament contained in the cartridge has expired.

In a second embodiment, the drug delivery device is a disposable device configured to be used with only a single cartridge. Here, the device is meant to be disposed, when the drug contained in the cartridge has been administered.

By providing a drug delivery device with the content display, the user can be informed on the type of the cartridge or the drug or composition of drugs contained in the cartridge.

As an example, at least one of the pieces of information comprises a name of a drug.

In particular, a first piece of information may comprise the name of a first drug and the second piece of information may comprise the name of a second drug. Alternatively or additionally, the pieces of information may comprise a marking or a coloring indicating a type of a cartridge or a drug contained in a cartridge.

In one embodiment, the content display is adjusted to display a certain piece of information before a cartridge is mounted in the drug delivery device. Thereby, the user is informed that the drug delivery device is dedicated to a specific type of cartridge or a specific drug contained in a cartridge and is guided to mount the corresponding cartridge.

In a second embodiment, the content display is adjusted during the mounting of a cartridge or when the cartridge is already mounted in the drug delivery device. Here, the user can be informed on the type of the cartridge or on the drug contained in the cartridge which is actually mounted in the device. Preferably, the content display permanently displays the appropriate piece of information as long as a certain cartridge is mounted in the device.

By providing a mechanically adjustable content display, the number of electronic parts in the drug delivery device can be reduced or the drug delivery device may even be completely free of electronic parts. Thereby, the drug delivery device may be manufactured at a low cost and work reliably. In addition to that, in a mechanical display, the information can be permanently displayed without consuming any power. Moreover, the device may be especially suitable for patients unfamiliar with or reluctant against electronic devices.

As an example, the content display may comprise a display member carrying the displayable information. The information may be printed or otherwise permanently applied to the display member. The display member may be partially covered, for example by a housing of the device, such that only a certain piece of information is visible for a user. Furthermore, the content display may comprise a display window for displaying a certain piece of information to a user. As an example, the display window may be an opening of a housing of the device through which an underlying part of a display member carrying a certain piece of information is visible.

For adjusting the content display to display a certain piece of information, the display member may be moveable, for example rotatable, relative to the display window. For adjusting the content display, the display member may be rotated by a defined amount of rotation until the desired piece of information is visible through the display window.

In one embodiment, the drug delivery device comprises locking means for permanently locking the content display to display one of the pieces of information.

By locking the content display, a further adjustment of the content display and, in particular, an accidental misadjustment is prevented. In one embodiment, the locking means non-releasably lock the content display such that the locking is irreversible. In a further embodiment, the locking may be reversible. Here, the locking means may be configured such that a specialist tool or a specialist action is required for unlocking the content display.

Furthermore, the drug delivery device may comprise an adjustment dial operable by a user. On operating the adjustment dial, the content display is adjustable to display one of the pieces of information.

In this case, the user may decide on the displayed piece of information. As an example, the content display may be adjusted to display a certain piece of information before a cartridge is mounted. Thereby, the drug delivery device can be dedicated to a specific cartridge such that the user is clearly guided to insert a specific cartridge type or a cartridge containing a specific drug in the device. The content display may be permanently locked after the adjustment. As an example, a healthcare professional may adjust the content display and lock the display before handing it over to a patient.

In order to prevent a further adjustment, the content display may be adjustable only once or only with a specialist tool provided to the healthcare professional. As an example, the locking means may comprise a frangible tab attached to a part of the content display which has to be moved for adjusting the content display. Here, after the content display is adjusted to display a specific piece of information by mechanically adjusting the content display with the tab, the frangible tab is removed. In a further embodiment, the locking means may comprise a clip being pressed into a unidirectional fixing once the display has been set.

The drug delivery device may comprise a main body and a mountable element. Here, the drug delivery device has an unmounted state, in which the mountable element is not mounted to the main body and a mounted state, in which the mountable element is mounted to the main body of the drug delivery device. In particular, the mountable element is one of a cartridge and a cartridge-retaining part.

Preferably, at least one of the main body and the mountable element comprise securing means for securing the mountable element to the main body.

In one embodiment, the securing means allow a releasable securing such that the mountable element can be mounted to and thereafter unmounted from the main body. In an alternative embodiment, the securing means are configured for non-releasably securing the mountable element to the main body.

The securing means may be configured for a screw-type connection of the mountable element and the main body. Here, the mountable element may comprise an outer thread which can be threadedly engaged with an inner thread of the main body. In this case, when screwing the mountable element to the main body, the mountable element carries out a combined translational and rotational movement relative to the main body.

In a further embodiment, the securing means may be configured for a bayonet-type connection of the mountable element and the main body. In this case, when connecting the mountable element to the main body, the mountable element may first carry out a translational movement and then a rotational movement relative to the main body.

In a further embodiment, the securing means may be configured for a clip-type connection such that the mountable element is pushed onto the main body and pressed into a unidirectional fixing at the main body.

In the case that the mountable element is a cartridge-retaining part, it may, at least partially, enclose a cartridge. In a reusable device, the cartridge may be releasably secured to the cartridge-retaining part such that the cartridge can be replaced and the cartridge-retaining part can be reused with a new cartridge. In a different embodiment of a reusable device, the cartridge is non-releasably secured to the cartridge-retaining part such that the cartridge is replaced together with the cartridge-retaining part.

In one embodiment, the main body of the device may comprise first coding means configured to allow the mounting of a certain type of cartridge or a cartridge containing a certain drug and prevent a mounting of non-matching cartridges. The mountable element may comprise second coding means configured for an interaction with the first coding means.

Preferably, the coding means are configured for a mechanical interaction such that the mounting of the mountable element is either allowed or prevented by the mechanical interaction. As an example, at least one of the first and second coding means comprise a protrusion. When mounting a matching mountable element to the cartridge, the protrusion may pass along a recess provided at the other one of the coding means. When trying to mount a non-matching mountable element to the main body, the protrusion may abut a part of the mountable element, whereby the mounting is blocked.

The first coding means may interact with the content display such that in a locked state of the content display only mountable elements having matching second coding means can be mounted to the main body. For mountable elements having non-matching second coding means, the mounting is prevented. Thus, the device can be dedicated to a certain type of cartridge by adjusting and thereafter locking the content display.

The mountable element may comprise an actuating member and the content display may comprise an adjustment member operable by the actuating member. The adjustment member is configured such that the content display is adjustable to display one of the pieces of information by operating the adjustment member with the actuating member.

Preferably, the actuating member is configured for a mechanical interaction with the adjustment member. Preferably, the actuating member is configured to exert a force on the adjustment member resulting in a movement of the adjustment member and thereby in an adjustment of the content display. In particular, the movement of the adjustment member may result in a movement of a display member carrying the displayable pieces of information. Here, the adjustment member may be an integral part of the display member.

The adjustment member may be operated by the actuating member on mounting the mountable element to the main body. In this case, the content display may be automatically adjusted to display a certain piece of information related to the mountable element, e. g. the type of the cartridge or the drug contained in the cartridge.

The displayed piece of information may be specific for one of the position of the actuating member on the mountable element and the shape of the actuating member.

As an example, the drug delivery device may be configured such that it is suitable for a plurality of different cartridges or a plurality of cartridges containing different drugs. Here, the position or the shape of the actuating member on the mountable element may be specific for the type of the cartridge or the drug contained in the cartridge such that the displayed piece of information is specific for the type of the cartridge or the drug contained in the cartridge.

Preferably, the position of the actuating member or the shape of the actuating member is adapted to the type of connection of the mountable element and the main body. In particular, the position or type of the actuating member is adapted to the relative movement of the mountable element and the main body in the mounting process.

As a first example, when the securing means are configured for a screw-type connection of the mountable element and the main body, the adjustment member may be configured to be driven by a relative rotational movement of the mountable element and the main body. Thereby, the rotation of the mountable element relative to the main body is used to drive the content display.

Here, the mountable element may have a longitudinal axis and the displayed piece of information may be specific for the angular position of the actuating member according to the longitudinal axis.

In particular, the angular position may determine the amount of rotation of the adjustment member when mounting the mountable element to the main body of the drug delivery device. The movement of the adjustment member may be directly transferred to a movement of a display member carrying the pieces of information. In a different embodiment, the adjustment member may be coupled to the display member via a gearing system such that the amount of rotation of the display member is different from the amount of rotation of the adjustment member. The gearing system applied may depend on the number of different coding options required and the font size in a display window.

As a second example, the securing means may be configured for a bayonet-type connection of the mountable element and the main body. Here, the adjustment member may be configured to be driven by a relative translational movement of the mountable element and the main body.

This type of adjustment mechanism may also be useful for a clip-type connection where the mountable element is pushed on the main body and secured by a unidirectional clip or other types of connections comprising a translational movement of the mountable element relative to the main body of the device. In this case, the amount of translational movement can be used to drive the content display.

The mountable element may have a longitudinal axis and the actuating member may extend along the longitudinal axis of the mountable element. The adjustment mechanism may be configured such that the displayed piece of information is specific for the length of the actuating member along the longitudinal axis.

Here, the length of the actuating member may determine the amount of translational movement of the adjustment member. The translational movement of the adjustment member may be transferred to a rotational movement of a display member.

The adjustment member may simultaneously serve as a first coding means for allowing the mounting of a mountable element having matching second coding means and preventing the mounting of mountable elements having non-matching second coding means. In a further embodiment, the adjustment member may interact with the first coding means such that a movement of the adjustment member will result in a movement of the coding means or vice versa.

The drug delivery device may comprise resilient means for biasing the display to a neutral display in an unmounted state of the drug delivery device.

In particular, a display member may be spring-loaded such that it is adjusted to the neutral display in the case that no sufficient counterforce is exerted on the display member. As an example, the neutral display may be a blank display or information not related to a specific cartridge or a specific drug. For example, the neutral display may indicate that the drug delivery device is ready for receiving a cartridge.

Moreover, a set of the drug delivery device as disclosed above and a plurality of mountable elements is provided. The plurality of mountable elements may be one of a plurality of cartridges or a plurality of cartridge-retaining parts mountable to the drug delivery device. The mountable elements differ in their shapes. The piece of information displayed by the content display is specific for the shape of the mountable element.

This embodiment may be particularly useful for a user administering different drugs. The user may be provided with a single drug delivery device having a main body and two or more cartridges comprising different drugs or different composition of drugs which can be mounted to the main body of the device. Here, the user is enabled to administer different drugs from one drug delivery device. As an example, the user may administer long-acting and short-acting insulin contained in different cartridges by using the same drug delivery device. The content display may inform the user on the type of a mounted cartridge or on the drug contained in a mounted cartridge.

Other features will become apparent from the following detailed description when considered in conjunction with the accompanying drawings.

BRIEF DESCRIPTION OF THE FIGURES

FIGS. 2A to 2G show the steps of manually adjusting the content display and mounting a matching and a non-matching cartridge to the drug delivery device according to FIG. 1, FIGS. 3A to 3G show a second embodiment of a drug delivery device and the steps of manually adjusting and locking the content display and attempting to mount a matching and a non-matching cartridge, FIGS. 4A to 4H show a third embodiment of a drug delivery device and the steps of mounting cartridges containing different drugs, FIGS. 5A and 5B show first embodiments of mountable elements configured for a screw-type connection, FIG. 5C shows a first embodiment of a display member configured for a screw-type connection, FIG. 5D shows a mechanical interaction of a mountable element according to FIG. 5A or 5B and a display member according to FIG. 5C, FIGS. 6A and 6B show second embodiments of mountable elements configured for a bayonet-type connection, FIG. 6C shows a second embodiment of a display member configured for a bayonet-type connection, FIG. 6D shows a mechanical interaction of a mountable element according to FIG. 6A or 6B and a display member according to FIG. 6C.

DETAILED DESCRIPTION

Figure 1:
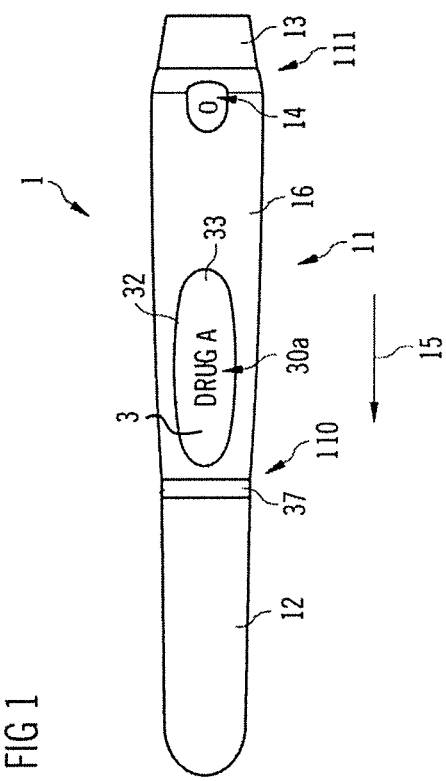
FIG. 1 shows a first embodiment of a drug delivery device comprising a content display operable by a user.

FIG. 1 shows a drug delivery device 1 having a main body 11 extending along a longitudinal axis 15. The drug delivery device 1 comprises a cartridge, wherein a liquid drug, for example an insulin drug, is contained.

The cartridge is secured to the main body 11 at a distal end 110 of the main body 11. The cartridge 21 is covered by a cap 12 attached to the main body 11. At its proximal end 111, the main body 11 comprises a dose element 13 for dialing and administering a dose of the drug. For dialing a dose, the dose element 13 is twisted relative to the main body 11. The size of the dialed dose is visible from a dose display 14. For injecting the dose, the dose element 13 is pushed towards the main body 11. Thereby, a drive mechanism drives a piston rod in a forward direction. The piston rod acts on a bung in the cartridge, whereby the liquid drug is pressed out through a needle unit.

The drug delivery device 1 comprises a content display 3 for informing the user on the type of the drug contained in the cartridge 21. The content display 3 comprises a display window 32, through which a piece of information 30a comprising the name of the drug contained in the cartridge is visible. The display window 32 is an opening in a housing 16 of the main body 11 and may be covered by a transparent material. As the display window 32 is located at the main body 11 of the drug delivery device 1, the drug name is visible also in the case that the cartridge is covered by the cap 12.

The displayable pieces of information 30a, 30b are provided on a display member 33. The display member 33 is covered by the housing 16 of the drug delivery device 1, except for the part where the piece of information 30a visible through the display window 32 is located. The display member 33 is a barrel carrying the names of all drugs suitable for use with the drug delivery device 1. Here, the drug delivery device 1 is suitable for two different drugs. For the purpose of this and the following examples, the drug names are indicated by "DRUG A" and "DRUG B", wherein, for example "DRUG A" may be a short-acting insulin and "DRUG B" may be a long-acting insulin.

Clearly, other drugs or composition of drugs could be used instead. Also, the drug delivery device 1 could be configured to be suitable for more than two possible drugs.

Alternatively or additionally to visually readable pieces of information, the content display may comprise tactually readable pieces of information for assisting visually impaired patients. In particular, the display member may comprise raised or lowered features indicating the type of a cartridge or the type of a drug contained in a cartridge. These raised or lowered features may be Braille or a simplified system for identifying a cartridge or a drug contained in the cartridge. Here, through the display window, a user may touch the part of the display member at which the specific piece of information is located. Thereby, a tactually readable content display is provided.

In addition, an audible piece of information may be provided in connection with the content display, for example a click feature indicating that a drug name is appearing in the window. In particular, the display member may click into place at distinct angular positions.

The drug names are provided at different angular positions at the display member 33 around the longitudinal axis 15 of the drug delivery device 1. By rotating the display member 33 by a defined amount of rotation, a specific piece of information 30a, including a specific drug name, is visible through the display window 32 and other pieces of information 30b are covered by the housing 16.

The content display 3 is mechanically adjusted to display a certain piece of information 30a by operating an adjustment member 34. Here, the adjustment member 34 is an adjustment dial 37 located at the distal end 110 of the main body 11. The adjustment dial 37 is a movable ring, operable by a user such that by rotating the adjustment dial 37 the piece of information 30a to be displayed can be selected. The adjustment dial 37 mechanically interacts with the display member 33 such that a rotation of the adjustment dial 37 results in a rotation of the display member 33.

FIGS. 2A to 2G show the steps of manually adjusting the content display 3 in a drug delivery device 1 according to FIG. 1 and thereafter mounting matching and non-matching cartridges 21a, 21b.

FIG. 2A shows the drug delivery device 1 as supplied by the manufacturer. The drug delivery device 1 is in its unmounted state 1b, wherein no cartridge is mounted. The content display 3 shows a neutral display 31. In particular, through the display window 32 a blank part of the display member 33 is visible.

FIG. 2B shows the drug delivery device 1 with the cap 12 removed. By twisting the adjustment dial 37, the user can adjust the content display 3 to display a selected piece of information 30a comprising a drug name. In particular, the rotation of the adjustment dial 37 relative to the main body 11 of the drug delivery device 1 results in a rotation of the display member 33 around the longitudinal axis 15 of the drug delivery device 1. On rotating the display member 33, the names of the drugs compatible with the drug delivery device 1 successively appear in the display window 32. The user selects the name of a drug by a defined amount of rotation of the adjustment dial 37.

FIG. 2C shows the step of mounting a cartridge 21a retained in a cartridge-retaining part 22a to the main body 11 of the drug delivery device 1. The cartridge-retaining part 22a is transparent such that a marking 23a provided on the cartridge 21a is visible. The marking 23a comprises the name of the drug contained in the cartridge 21a. The drug name matches the drug name displayed by the display window 32 indicating that the cartridge 21a matches the selection of the user. The cartridge 21a is transparent such that the bung 27 indicating the filling status of the cartridge 21a is visible.

The cartridge-retaining part 22a is configured for a screw-type connection with the main body 11. At its proximal end 201, the cartridge-retaining part 22a comprises an outer thread engageable with an inner thread at the distal end 110 of the main body 11. For securing the cartridge-retaining part 22a to the main body 11, the cartridge-retaining part 22a is screwed onto the main body 11, thereby carrying out a combined translational and rotational movement relative to the main body 11.

FIG. 2D shows the drug delivery device 1 in its mounted state 1a, wherein the cartridge-retaining part 22a comprising the cartridge 21a is mounted to the main body 11.

Figure 2E:
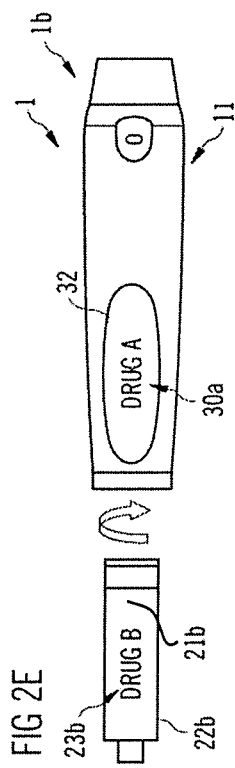

FIG. 2E shows the drug delivery device 1 again in its unmounted state 1b. Here, a user mounts a non-matching cartridge 21b to the main body 11, which can be seen by the differing drug names "DRUG B" shown by the marking 23b on the cartridge 21b and the drug name "DRUG A" shown by the display window 32.

Figure 2F:
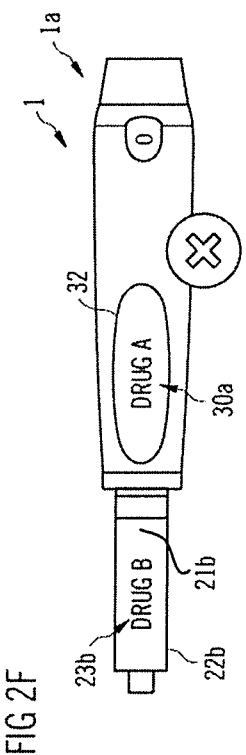

FIG. 2F shows the drug delivery device 1, wherein the non-matching cartridge 21b is mounted to the main body 11. In this embodiment, the mounting of the non-matching cartridge 21b is not prevented. The cartridge retaining part 22a containing a cartridge 21a with a matching drug as shown in FIG. 2D does not differ from the cartridge retaining part 22b containing a cartridge 21b with a non-matching drug.

Figure 2G:
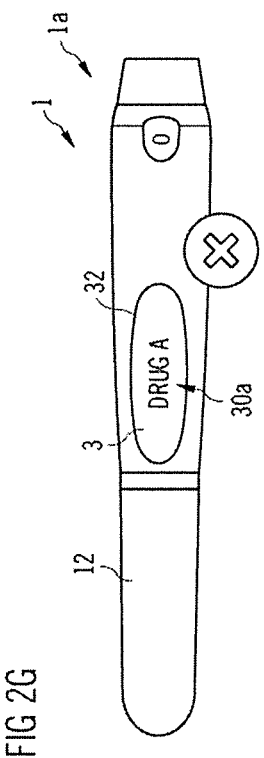

FIG. 2G shows the drug delivery device 1 in its mounted state 1a with the cap 12 in place. The cap 12 covers the marking 23b on the cartridge 21b. The drug name "DRUG A" is visible through the display window 32. In this most simple embodiment, it is not ensured that the drug name visible through the display window 32 corresponds to the drug contained in the cartridge 21b.

FIGS. 3A to 3G show a second embodiment of a drug delivery device 1, where the mounting of a non-matching cartridge 21b can be prevented. The drug delivery device 1 comprises an adjustment dial 37 operable by a user or by a manufacturer.

FIG. 3A shows the drug delivery device 1 in its unmounted state 1b, wherein no cartridge is mounted to the main body 11 of the drug delivery device 1. The display window 32 shows a neutral display 31.

The drug delivery device 1 comprises locking means for locking the content display 3. As examples, the locking means can be operated by a user or by a manufacturer before delivering the drug delivery device 1. In the latter case, the manufacturing plant may use the same device assembly, but set to display different products.

The locking means comprise a button 350 coupled to a unidirectional clip which can be pressed into a unidirectional fixing in the housing 16 of the main body 11. The locking means block the content display 3 such that a further movement of the display member 33 is prevented. Thereby, the content display 3 is locked to permanently display a specific piece of information 30a, 30b or a neutral display 31. Accordingly, the drug delivery device 1 is permanently dedicated to a specific drug.

FIGS. 3B and 3C show the drug delivery device 1 with the cap 12 removed. By twisting the adjustment dial 37, the content display 3 can be adjusted to display a selected piece of information 30a, 30b. In particular, depending on the amount of rotation of the display member 33, one of the drug names "DRUG A", "DRUG B", appears in the display window 32.

FIG. 3C shows the content display 3 displaying the drug name "DRUG A", which is the drug selected by the user. To confirm the selection, the user presses the button 350 of the locking means into the housing 16, thereby locking the content display 3.

The drug delivery device 1 comprises coding means for allowing a mounting of a matching cartridge 21a and preventing a mounting of a non-matching cartridge 21b. On adjusting the content display 3, first coding means on the display member 33 are adjusted such that a mountable element 2a having second coding means matching the adjusted first coding means is mountable, whereas a mountable element 2b having non-matching second coding means is not mountable to the drug delivery device 1.

FIG. 3D shows an attempted mounting of a cartridge 21b retained in a cartridge-retaining part 22b, wherein the drug contained in the cartridge 21b, "DRUG B", does not match the drug name, "DRUG A", visible through the display window 32. Accordingly, the second coding means do not match the adjusted first coding means. Thus, by the mechanical interaction of the first coding means and the second coding means a mounting of the non-matching mountable element 2b is blocked.

FIG. 3E shows a mounting of a cartridge 21a contained in a cartridge-retaining part 22a, wherein the drug, "DRUG A" contained in the cartridge corresponds to the name, "DRUG A", visible through the display window 32. In this case, the mountable element comprises second coding means matching the adjusted first coding means. Thereby, a mounting of the mountable element 2a is allowed.

FIG. 3F shows the drug delivery device 1 in its mounted state 1a, wherein a matching cartridge 21a is mounted to the main body 11.

FIG. 3G shows the drug delivery device 1 according to FIG. 3F with the cap 12 attached. The name of the drug contained in the cartridge 21a is visible through the display window 32. In this embodiment, the mechanical interaction of first and second coding means ensure that the correct cartridge 21a is mounted.

FIGS. 4A to 4H show a third embodiment of a drug delivery device 1, wherein the content display 3 is mechanically adjustable by an actuating member at the mountable element 2a, 2b.

Figure 4A:
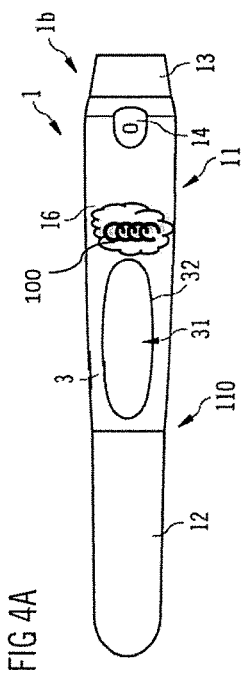

FIG. 4A shows the drug delivery device 1 in its unmounted state 1b, wherein no cartridge is mounted. The display window 32 shows a neutral display 31. The main body 11 of the device comprises biasing means biasing the content display 3 to show a neutral display 31 in the unmounted state 1b.

At the distal end 110 of the main body 11, the content display 3 comprises an adjustment member operable by an actuating member at the mountable element 2a, 2b.

Figure 4B:
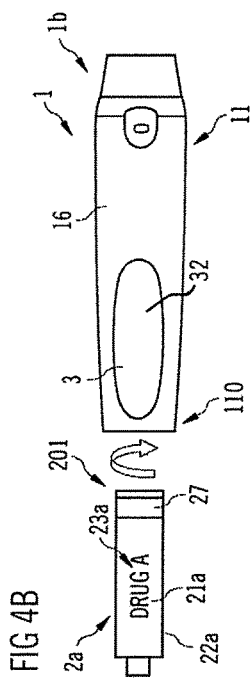

FIG. 4B shows the step of mounting a cartridge 21a contained in a cartridge-retaining part 22a to the main body 11 of the drug delivery device 1. The drug delivery device 1 is configured for a screw-type connection. At its proximal end 201, the cartridge-retaining part 22a comprises an outer thread which engages with an inner thread located at the distal end 110 of the main body 11. Furthermore, at its proximal end 201, the cartridge-retaining part 22a comprises an actuating member operating an adjustment member of the content display 3. The position of the actuating member on the mountable element 2a is specific for the drug contained in the cartridge 21a. By the mechanical interaction of the actuating member and the adjustment member, the content display 3 is adjusted to display the piece of information 30a corresponding to the drug contained in the cartridge 21a.

Figure 4C:
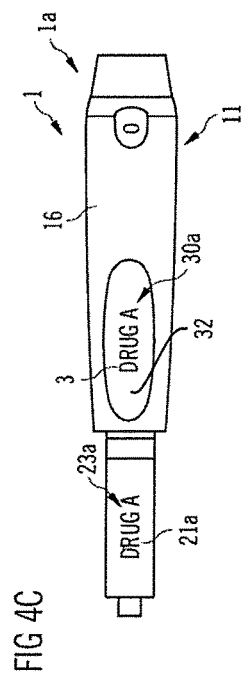

FIG. 4C shows the drug delivery device 1 in its mounted state 1a, wherein the cartridge 21a is mounted to the main body 11. The piece of information 30a visible through the display window 32 comprises the drug name "DRUG A" matching the drug name "DRUG A" shown by the marking 23a on the cartridge 21a. Thus, by mounting the cartridge 21a to the drug delivery device 1, the name of the drug contained in the cartridge 21a is automatically displayed in the display window 32.

Figure 4D:
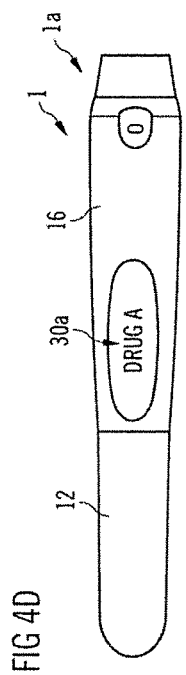

FIG. 4D shows the drug delivery device 1 in its mounted state 1a with the cap 12 attached. The cap 12 covers the cartridge 21a such that the marking 23a provided at the cartridge 21a is not visible from outside. The name of the drug contained in the cartridge 21a is visible through the display window 32.

FIG. 4E shows the step of removing an empty cartridge 21a from the main body 11 of the drug delivery device 1. The bung 27 inside the cartridge 21a is located at the distal end 200 of the mountable element 2a. This shows that the drug has been fully pressed out of the cartridge 21a. When unmounting the cartridge 21a, the biasing means trigger the content display 3 to return to a neutral display 31. In particular, the display member 33 is spring-loaded via spring 100 when a cartridge 21a is mounted.

FIG. 4F shows the step of mounting a cartridge 21b containing a different drug than the drug contained in the empty cartridge 21a according to FIG. 4E. The cartridge retaining part 22b is provided with an actuating member specific for the drug contained in the cartridge 21b.

FIG. 4G shows the drug delivery device 1 in its mounted state 1a, wherein the new cartridge 21b is mounted to the main body. On mounting the cartridge 21b, the content display 3 is automatically adjusted to show the appropriate piece of information 30b corresponding to the drug contained in the cartridge 21b. In the case that the cartridge 21b containing a specific drug was deliberately mounted to the drug delivery device 1, the content display 32 confirms the user selection of the cartridge 21b. In the case that a wrong cartridge 21b was inadvertently mounted, the user is warned by the content display 3 of his mistake.

FIG. 4H shows the drug delivery device 1, wherein the cap 12 is attached to the main body 11 of the device. With the cap 12 in place the name of the drug, "DRUG B", is visible from the outside through the display window 32.

FIGS. 5A and 5B show first embodiments of mountable elements 2a, 2b usable with a drug delivery device 1 as shown in FIGS. 4A to 4H. Each of the mountable elements 2a, 2b comprises a cartridge-retaining part 22a, 22b, wherein a cartridge 21a, 21b comprising a liquid medicament is contained. The cartridge-retaining parts 22a, 22b are configured for a screw-type connection and comprise securing means in the form of outer threads 61 located at the proximal end 201 of the mountable element 2a, 2b.

The drug contained in the cartridge 21a shown in FIG. 5A is different from the drug contained in the cartridge 21b shown in FIG. 5B, which can be seen from the different markings 23a, 23b, "DRUG A" and "DRUG B", on the cartridges 21a, 21b.

At its proximal end 201, each cartridge-retaining part 22a, 22b comprises an actuating member 26a, 26b for adjusting the content display 3 at the main body 11 of the drug delivery device 1. The angular position 261a, 261b of the actuating member 26a, 26b around the longitudinal axis 25 is specific for the drug contained in the cartridge 21a, 21b.

FIG. 5C shows a first embodiment of a display member 33 located in the housing 16 of a drug delivery device 1. For clarity reasons, the main body of the drug delivery device 1 is not shown here. Near the distal end 110 of the main body 11, the display member 33 is provided with an adjustment member 34. The adjustment member 34 is an integral part of the display member 33 and comprises a contact surface 36 for mechanical interaction with the actuating members 26a, 26b of the mountable elements 2a, 2b as shown in FIGS. 5A and 5B. The display member 33 is a barrel carrying different pieces of information 30a, 30b comprising the names of the drugs, "DRUG A", "DRUG B", compatible with the drug delivery device 1. The drug names are printed on the outer surface of the display member 33. In a different embodiment, the drug names may be provided on a label applied to the display member 33.

FIG. 5D shows a mechanical interaction of one of the mountable elements 2a, 2b according to FIGS. 5A and 5B and a display member 33 according to FIG. 5C. The main body 11 of the drug delivery device 1 and the display window 32 are depicted by dotted lines.

The main body 11 of the drug delivery device 1 comprises an inner thread which engages with the outer thread 61 of the mountable element 2a, 2b. On mounting the mountable element 2a, 2b to the main body 11, the mountable element 2a, 2b carries out a rotational movement relative to the main body 11. After a predefined amount of rotation, depending on the angular position 261a, 261b of the actuating member 26a, 26b, the actuating member 26a, 26b abuts the contact surface 36 of the adjustment member 34. On a further rotation of the mountable element 2a, 2b relative to the main body 11, the actuating member 26a, 26b drives the adjustment member 34, whereby the adjustment member 34 and the display member 33 carry out a rotational movement relative to the main body 11.

When the mountable element 2a, 2b has been fully screwed onto the main body 11, the rotation stops and a predefined part of the display member 33 is visible through the display window 32. The angular position 261a, 261b of the actuating member 26a, 26b on the mountable element 2a, 2b is chosen such that the rotation comes to an end when the drug name matching the drug contained in the cartridge 21a, 21b appears in the display window 32.

Accordingly, the rotation of the mountable element 2a, 2b is used to drive the rotation of the display member 33 and thereby it is used for the adjustment of the content display 3.

In a further embodiment, the drug delivery device 1 may contain a spring that is charged by the insertion of the cartridge retaining part 22a, 22b and causes the display member 33 to rotate to an angular end stop. The amount of charge and, thereby, the amount of rotation is determined by the position of an actuating member 26a, 26b on the mountable element 2a, 2b.

FIGS. 6A and 6B show second embodiments of mountable elements 2a, 2b comprising actuating members 26a, 26b. Here, the drug delivery device 1 is configured for a bayonet-type connection of the mountable elements 2a, 2b and the main body 11. Each of the mountable elements 2a, 2b comprises a cartridge-retaining part 22a, 22b, wherein a cartridge 21a, 21b comprising a liquid medicament is contained.

The drug contained in the cartridge 21a shown in FIG. 6A is different from the drug contained in the cartridge 21b shown in FIG. 6B, which can be seen from the different markings 23a, 23b on the cartridges 21a, 21b.

At their proximal ends 201, the cartridge retaining parts 22a, 22b comprise securing means in forms of lugs 62. A groove 63 is provided at an inner part of the housing 16 of the drug delivery device 1, in which the lug 62 is guided on mounting the mountable elements 2a, 2b to the main body 11.

At its proximal end 201, each cartridge-retaining part 22a, 22b comprises an actuating member 26a, 26b for adjusting the content display 3 at the main body 11 of the drug delivery device 1. The lengths 260a, 260b of the actuating members 26a, 26b, that means their extensions 260a, 260b along the longitudinal axis 25 of the mountable element 2a, 2b, is specific for the drug contained in the cartridge 21a, 21b. In particular, the length 260b of the actuating member 26b at the cartridge retaining part 22b shown in FIG. 6B is larger than the length 260a of the actuating member 26a at the cartridge retaining part 22a shown in FIG. 6A. Thus, the different drugs are encoded by the different lengths 260a, 260b of the actuating members 26a, 26b.

FIG. 6C shows a display member 33 usable with a mountable element 2a, 2b shown in FIGS. 6A and 6B. The display member 33 is part of the main body 11 of the drug delivery device 1. For clarity reasons, the main body is not depicted here.

The display member 33 is provided with pieces of information 30a, 30b comprising the drug names compatible with the drug delivery device 1. At the distal end 110 of the main body 11, the display member 33 comprises an adjustment member 34 configured for a mechanical interaction with the actuating member 26a, 26b of the mountable element 2a, 2b. In particular, the adjustment member 34 comprises a camming contact surface 36.

FIG. 6D shows a mechanical interaction of a mountable element 2a, 2b according to FIG. 6A or 6B and a display member 33 according to FIG. 6C.

The drug delivery device 1 is configured for a bayonet-connection such that on mounting the mountable element 2a, 2b to the main body 11, the mountable element 2a, 2b is pushed on the main body 11 and then twisted relative to the main body 11. Thus, the mounting comprises a relative translational movement followed by a rotational movement of the mountable element 2a, 2b and the main body 11. The lug 62 at the proximal end 201 of the mountable element 2a, 2b is guided in a groove 63 provided in an inner part of the housing 16 of the main body 11.

The translational movement of the mountable element 2a, 2b is used for driving the display member 33 of the content display 3. In particular, at a defined relative axial position of the mountable element 2a, 2b and the main body 11, the actuating member 26a, 26b abuts the contact surface 36 at the adjustment member 34. The length 260a, 260b of the actuating member 26a, 26b determines the relative axial position at which a contact between the adjustment member 34 and the actuating member 26a, 26b occurs. By the abutment of the actuating member 26a, 26b and the camming contact surface 36, the translational movement of the mountable element 2 results in a rotational movement of the display member 33.

As the length 260a, 260b of the actuating member 26a, 26b determines the amount of translational movement of the mountable element 2a, 2b prior to the contact between the actuating member 26a, 26b and the contact surface 36, it also determines the amount of translational movement which remains until the mountable element 2a, 2b is fully mounted. Thereby, the length 260a, 260b defines the amount of rotation of the display member 33. The length 260a, 260b is chosen such that the display member 33 is rotated until the name of the drug contained in the cartridge 21a, 21b appears in the display window 32.

In further embodiments, the display member is not directly driven by the actuating member but through a geared coupling. This may help to improve display resolution and increase the amount of options of the interaction of the mountable element and the content display.

The actuating members 26a, 26b shown in FIGS. 5A, 5B, 6A and 6B could alternatively or additionally serve as second coding means interacting with first coding means at the main body 11 of the drug delivery device 1. Thereby, it may be ensured that only specific cartridges 21a, 21b and, in particular, cartridges 21a, 21b containing the drug selected by the content display 3 can be mounted. Here, the adjustment member 34 may serve as first coding means 38. When adjusting the content display 3, the adjustment member 34 is moved to a specific angular position relative to the longitudinal axis 15 of the drug delivery device 1. When locking the content display 3, a further rotational movement of the adjustment member 34 is prevented. The mechanical interaction of the actuating member 26a, 26b and the adjustment member 34 then prevents the full mounting of non-matching mountable elements 2b and allows the mounting of matching mountable elements 2a. In this embodiment, the content display 3 may be configured for a manual adjustment or for an adjustment by mechanical interaction with a mountable element 2a, 2b.

In further embodiments, at least one of the actuating members, adjustment members, first and second coding means may comprise ribs, grooves, angled cut-outs or castellations or other features suitable for a mechanical interaction. Furthermore, different actuating members and second coding means may be provided by different lengths, different outer or different inner diameters of mountable elements or components added to mountable elements. Here, a certain length or diameter may be specific for a certain drug or a certain type of cartridge. Similarly, different adjustment members and first coding means may be provided by different lengths or different outer or different inner diameters of elements at the main body or components added to the main body.

In the case of a screw-type connection, different actuating members and second coding means may be provided by different screw thread pitches. In the case of a bayonet-type connection, different actuating members and second coding means may be provided by different bayonet fitting features.

In further embodiments, the mountable element may not comprise a cartridge-retaining part. Here, the cartridge may be configured to be directly attached to the main body. The actuating member and the second coding means may be provided by a ring made of a suitable material permanently attached to the cartridge.

The terms "drug" and "medicament", as used herein, mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N- palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A drug delivery device configured to receive a cartridge containing a drug, the drug delivery device comprising a dose display for displaying a size of a set dose of the drug and a mechanically adjustable content display for displaying information related to one of the cartridge and the drug contained in the cartridge,
wherein the adjustable content display is configured to selectively display at least two different pieces of information and wherein the adjustable content display is configured such that one of the at least two different pieces of information is displayed only through direct mechanical adjustment of the adjustable content display without consuming electrical power from the drug delivery device, and where the dose display and the adjustable content display are two separate displays positioned at different locations on the drug delivery device, wherein the drug delivery device further comprises a main body and a mountable element, the drug delivery device having an unmounted state, in which the mountable element is not mounted to the main body, and a mounted state, in which the mountable element is mounted to the main body, wherein the mountable element is one of the cartridge and a cartridge retaining part, wherein the mountable element comprises an actuating member, wherein an adjustment member is operable by the actuating member and wherein the adjustable content display is adjustable to display one of the pieces of information by operating the adjustment member with the actuating member, wherein at least one of the main body and the mountable element comprise a connector configured to secure the mountable element to the main body, wherein the connector is configured for a screw-type connection of the mountable element and the main body and wherein the adjustment member is configured to be driven by a relative rotational movement of the mountable element and the main body.

2. The drug delivery device according to claim 1, wherein at least one of the pieces of information comprises a name of a drug.

3. The drug delivery device according to claim 1 comprising a lock configured to permanently lock the content display to display one of the pieces of information.

4. The drug delivery device according to claim 1,
wherein the mountable element has a longitudinal axis and
wherein the displayed piece of information is specific for the angular position of the actuating member according to the longitudinal axis.

5. The drug delivery device according to claim 1 comprising a resilient member directly connected to the content display to maintain the content display in a neutral display in an unmounted state of the drug delivery device.

6. The drug delivery device according to claim 1 comprising coding elements configured to allow the mounting of a certain type of cartridge or a cartridge containing a certain drug and configured to prevent a mounting of a non-matching cartridge.

7. A set of the drug delivery device according to claim 1 and a plurality of mountable elements,
wherein the plurality of mountable elements is one of a plurality of cartridges and a plurality of cartridge retaining parts mountable to the drug delivery device,
wherein the mountable elements differ in their shapes and
wherein the displayed piece of information is specific for the shape of the mountable element.

8. A drug delivery device configured to receive a cartridge containing a drug, the drug delivery device comprising a dose display for displaying a size of a set dose of the drug and a mechanically adjustable content display for displaying information related to one of a specific type of drug, and a specific composition of the drug contained in the cartridge
wherein the content display is configured to selectively display at least two different pieces of information and
wherein the content display is configured such that one of the at least two different pieces of information is displayed only through direct mechanical adjustment of the content display without consuming electrical power from the drug delivery device, and where the dose display and the content display are two separate displays positioned at different locations on the drug delivery device, wherein the drug delivery device comprises a main body and a mountable element, the drug delivery device having an unmounted state in which the mountable element Is not mounted to the main body, and a mounted state, in which the mountable element is mounted to the main body, wherein the mountable element is one of a cartridge and a cartridge retaining part, wherein the main body comprises a first coding means and the mountable element comprises a second coding means and wherein by adjusting the content display the first coding means are adjusted such that the mountable element is mountable if the second coding means matches an adjusted first coding means and a mounting is blocked by a mechanical interaction of the first coding means and the second coding means if the second coding means does not match the adjusted first coding means.

9. The drug delivery device according to claim 8 comprising an adjustment dial operable by a user, wherein the content display is adjustable to display one of the pieces of information by operating the adjustment dial.

10. The drug delivery device according to claim 8,
wherein the mountable element comprises an actuating member,
wherein the content display comprises an adjustment member operable by the actuating member and
wherein the content display is adjustable to display one of the pieces of information by operating the adjustment member with the actuating member.

11. The drug delivery device according to claim 10, wherein the displayed piece of information is specific for one of the position of the actuating member on the mountable element and the shape of the actuating member.

12. A drug delivery device configured to receive a cartridge containing a drug, the drug delivery device comprising a dose display for displaying a size of a set dose of the drug and a mechanically adjustable content display for displaying information related to one of the cartridge and the drug contained in the cartridge,
wherein the adjustable content display is configured to selectively display at least two different pieces of information and wherein the adjustable content display is configured such that one of the at least two different pieces of information is displayed only through direct mechanical adjustment of the adjustable content display without consuming electrical power from the drug delivery device, and where the dose display and the adjustable content display are two separate displays positioned at different locations on the drug delivery device, wherein the drug delivery device further comprises a main body and a mountable element, the drug delivery device having an unmounted state, in which the mountable element is not mounted to the main body, and a mounted state, in which the mountable element is mounted to the main body, wherein the mountable element is one of the cartridge and a cartridge retaining part, wherein the mountable element comprises an actuating member, wherein an adjustment member is operable by the actuating member and wherein the adjustable content display is adjustable to display one of the pieces of information by operating the adjustment member with the actuating member, wherein at least one of the main body and the mountable element comprise a connector configured to secure the mountable element to the main body wherein the connector is configured for a bayonet-type connection of the mountable element and the main body and wherein the adjustment member is configured to be driven by a relative translational movement of the mountable element and the main body.

13. The drug delivery device according to claim 12, wherein the mountable element has a longitudinal axis, wherein the actuating member extends along the longitudinal axis of the mountable element and wherein the displayed piece of information is specific for the length of the actuating member along the longitudinal axis.

* * * * *